United States Patent
Dadey et al.

(10) Patent No.: US 9,561,282 B2
(45) Date of Patent: Feb. 7, 2017

(54) LOW-BURST POLYMERS AND METHODS TO PRODUCE POLYMER

(71) Applicant: Tolmar Therapeutics, Inc., Fort Collins, CO (US)

(72) Inventors: Eric Dadey, Furlong, PA (US); John Middleton, Birmingham, AL (US); Richard L. Norton, Ft. Collins, CO (US)

(73) Assignee: Tolmar Therapeutics, Inc., Fort Collins, CO (US)

( * ) Notice: Subject to any disclaimer, the term of this patent is extended or adjusted under 35 U.S.C. 154(b) by 0 days.

(21) Appl. No.: 14/924,243

(22) Filed: Oct. 27, 2015

(65) Prior Publication Data

US 2016/0106847 A1 Apr. 21, 2016

Related U.S. Application Data

(62) Division of application No. 12/527,377, filed as application No. PCT/US2008/001887 on Feb. 13, 2008, now Pat. No. 9,187,593.

(60) Provisional application No. 60/901,435, filed on Feb. 15, 2007.

(51) Int. Cl.
| | |
|---|---|
| *A61K 47/34* | (2006.01) |
| *A61K 38/08* | (2006.01) |
| *A61K 38/12* | (2006.01) |
| *C08G 63/08* | (2006.01) |
| *C08G 63/90* | (2006.01) |
| *A61K 9/00* | (2006.01) |

(52) U.S. Cl.
CPC ............ *A61K 47/34* (2013.01); *A61K 38/08* (2013.01); *A61K 38/12* (2013.01); *C08G 63/08* (2013.01); *C08G 63/90* (2013.01); *A61K 9/0024* (2013.01)

(58) Field of Classification Search
None
See application file for complete search history.

(56) References Cited

U.S. PATENT DOCUMENTS

| | | | |
|---|---|---|---|
| 4,728,721 A * | 3/1988 | Yamamoto | A61K 9/1647 528/354 |
| 4,810,775 A | 3/1989 | Bendix et al. | |
| 4,960,866 A | 10/1990 | Bendix et al. | |
| 5,278,201 A | 1/1994 | Dunn et al. | |
| 5,278,202 A | 1/1994 | Dunn et al. | |
| 5,324,519 A | 6/1994 | Dunn et al. | |
| 5,340,849 A | 8/1994 | Dunn et al. | |
| 5,487,897 A | 1/1996 | Polson et al. | |
| 5,585,460 A | 12/1996 | Yamada et al. | |
| 5,599,552 A | 2/1997 | Dunn et al. | |
| 5,681,873 A | 10/1997 | Norton et al. | |
| 5,702,716 A | 12/1997 | Dunn et al. | |
| 5,733,950 A | 3/1998 | Dunn et al. | |
| 5,736,152 A | 4/1998 | Dunn | |
| 5,739,176 A | 4/1998 | Dunn et al. | |
| 5,744,153 A | 4/1998 | Yewey et al. | |
| 5,759,563 A | 6/1998 | Yewey et al. | |
| 5,780,044 A | 7/1998 | Yewey et al. | |
| 5,792,469 A | 8/1998 | Tipton et al. | |
| 5,945,115 A | 8/1999 | Dunn et al. | |
| 5,990,194 A | 11/1999 | Dunn et al. | |
| 6,143,314 A | 11/2000 | Chandrashekar et al. | |
| 6,261,583 B1 | 7/2001 | Dunn et al. | |
| 6,264,970 B1 | 7/2001 | Hata et al. | |
| 6,355,657 B1 | 3/2002 | Osborne | |
| 6,395,293 B2 | 5/2002 | Polson et al. | |
| 6,461,631 B1 | 10/2002 | Dunn et al. | |
| RE37,950 E | 12/2002 | Dunn et al. | |
| 6,528,080 B2 | 3/2003 | Dunn et al. | |
| 6,565,874 B1 | 5/2003 | Dunn et al. | |
| 6,696,500 B2 | 2/2004 | Hata et al. | |
| 6,773,714 B2 | 8/2004 | Dunn et al. | |
| 7,019,106 B2 | 3/2006 | Yamamoto et al. | |
| 8,486,455 B2 | 7/2013 | Dunn et al. | |
| 9,187,593 B2 | 11/2015 | Dadey et al. | |
| 2002/0098238 A1* | 7/2002 | Prikoszovich | A61K 9/1647 424/486 |
| 2003/0153724 A1 | 8/2003 | Yamamoto et al. | |
| 2004/0241229 A1 | 12/2004 | Yamamoto et al. | |
| 2006/0034889 A1* | 2/2006 | Jo | A61K 9/0024 424/426 |
| 2006/0210604 A1* | 9/2006 | Dadey | A61F 9/0008 424/427 |

(Continued)

FOREIGN PATENT DOCUMENTS

| | | |
|---|---|---|
| CA | 2214889 A1 | 9/1996 |
| EP | 2115029 B1 | 9/2015 |

(Continued)

OTHER PUBLICATIONS

"U.S. Appl. No. 12/527,377, Examiner Interview Summary mailed Apr. 20, 2015", 3 pgs.
"U.S. Appl. No. 12/527,377, Final Office Action mailed Oct. 15, 2012", 10 pgs.
"U.S. Appl. No. 12/527,377, Non Final Office Action mailed Jan. 2, 2015", 12 pgs.
"U.S. Appl. No. 12/527,377, Non Final Office Action mailed Mar. 1, 2012", 11 pgs.
"U.S. Appl. No. 12/527,377, Non Final Office Action mailed Mar. 11, 2014", 9 pgs.
"U.S. Appl. No. 12/527,377, Notice of Allowance mailed Jul. 22, 2015", 10 pgs.
"U.S. Appl. No. 12/527,377, Response filed Jan. 22, 2013 to Final Office Action mailed Oct. 15, 2012", 11 pgs.

(Continued)

*Primary Examiner* — Ali Soroush
*Assistant Examiner* — Genevieve S Alley
(74) *Attorney, Agent, or Firm* — Sheridan Ross, P.C.

(57) ABSTRACT

A PLG copolymer material, termed a PLG(p) copolymer material, adapted for use in a controlled release formulation for a bioactive material is provided, wherein the formulation exhibits a reduced "initial burst" effect when introduced into the tissue of a patient in need thereof. A method of preparation of the PLG copolymer material is also provided, as are methods of use.

10 Claims, 1 Drawing Sheet

(56) References Cited

U.S. PATENT DOCUMENTS

2008/0108778 A1    5/2008    Yamatomo et al.

FOREIGN PATENT DOCUMENTS

| JP | 08169818 A | 7/1996 |
|----|------------|--------|
| JP | 1072375 A | 3/1998 |
| JP | 10072375 A | 3/1998 |
| JP | 2002516910 A | 6/2002 |
| JP | 2004256546 A | 9/2004 |
| JP | 2004510807 A | 4/2008 |
| WO | WO-9918142 A1 | 4/1999 |
| WO | WO-0230393 A2 | 4/2002 |
| WO | WO-2006053175 A2 | 5/2006 |
| WO | WO-2008045516 A1 | 4/2008 |
| WO | WO-2008100532 A1 | 8/2008 |

OTHER PUBLICATIONS

"U.S. Appl. No. 12/527,377, Response filed Apr. 13, 2015 to Non Final Office Action mailed Jan. 2, 2015", 7 pgs.
"U.S. Appl. No. 12/527,377, Response filed Jun. 15, 2012 to Non Final Office Action mailed Mar. 1, 2012", 11 pgs.
"U.S. Appl. No. 12/527,377, Response filed Sep. 10, 2014 to Non Final Office Action mailed Mar. 11, 2014", 6 pgs.
"U.S. Appl. No. 12/527,377, Response filed Nov. 7, 2011 to Restriction Requirement mailed Oct. 12, 2011", 7 pgs.
"U.S. Appl. No. 12/527,377, Restriction Requirement mailed Oct. 12, 2011", 8 pgs.
"Canadian Application Serial No. 2,678,350, Office Action mailed Jul. 31, 2014", 3 pgs.
"Canadian Application Serial No. 2,678,350, Office Action mailed Nov. 20, 2013", 4 pgs.
"Canadian Application Serial No. 2,678,350, Office Action mailed Dec. 18, 2014", 3 pgs.
"Canadian Application Serial No. 2,678,350, Response filed Feb. 19, 2015 to Office Action mailed Dec. 18, 2014", 57 pgs.
"Canadian Application Serial No. 2,678,350, Response filed May 20, 2014 to Office Action mailed Nov. 20, 2013", 30 pgs.
"European Application Serial No. 08725511.3, Examination Notification Art. 94(3) mailed Feb. 27, 2013", 3 pgs.
"European Application Serial No. 08725511.3, Response filed Aug. 21, 2013 to Examination Notification Art. 94(3) mailed Feb. 27, 2013", 5 pgs.
"International Application Serial No. PCT/US2008/001887, International Preliminary Report on Patentability dated Aug. 19, 2009", 6 pgs.
"International Application Serial No. PCT/US2008/001887, International Search Report mailed Jul. 1, 2008", 5 pgs.
"International Application Serial No. PCT/US2008/001887, Written Opinion mailed Jul. 1, 2008", 6 pgs.
"Japanese Application Serial No. 2009-550095, Office Action mailed Dec. 18, 2012", 7 pgs.
"Japanese Application Serial No. 2009-550095, Response filed Mar. 15, 2013 to Office Action mailed Dec. 18, 2012", (w/ English Amended Claims), 17 pgs.
"Japanese Application Serial No. 2013-166807, Response filed Aug. 14, 2014 tp Office Action mailed May 21, 2014", (w/ English Translation of Amended Claims), 15 pgs.
"Japanese Application Serial No. 2013-166807, Final Office Action mailed Dec. 26, 2014", 3 pgs.
"Japanese Application Serial No. 2013-166807, Office Action mailed May 21, 2014", 8 pgs.
Ding, A. G, et al., "Determination of water-soluble acid distribution in poly(lactide-co-glycolide)", Journal of Pharmaceutical Sciences, 93(2), (Feb. 2004), 322-331.
Lisinsky, George, "Solvent Miscibility Chart", Beloit College, (Accessed Feb. 21-23, 2012), 1 pg.
Ottenbrite, Raphael M, et al., Polymeric Drugs & Drug Delivery Systems, Technomic Publishing Company, (2001).
Park, Tae Gwan, "Chapter 7. Bioconjugation of Biodegradable Poly (lactic/glycolic acid)to Protein,Peptide, and Anti-Cancer Drug", Polymeric Drugs and Drug Delivery Systems, Edited by Raphael M . Ottenbrite and Sung Wan Kim, CRC Press, (2000), 101-114.
"European Application Serial No. 15185218.3, Communication Pursuant to Rule 55 EPC mailed Jan. 11, 2016", 2 pgs.
Ding, A. G, et al., "Determination of water-soluble acid distribution in poly(lactide-co-glycolide)", Journal of Pharmaceutical Sciences, 93(2), (Feb. 2004), 322-331, only p. 328-331.
Holding, Steve, "Characterisation of Polymers Using Gel Permeation Chromatography and Associated Techniques", Chromatography Today Nov. / Dec. 2011, (2011), 4-8.
Schliecker, G., et al., "Characterization of a homologous series of D,L-lactic acid oligomers; a mechanistic study on the degradation kinetics in vitro", Biomaterials, 24(21), (Sep. 2003), 3835-44.

* cited by examiner

Figure 1. ATRS-956 Study % Release of Octreotide After 1 and 21 Days
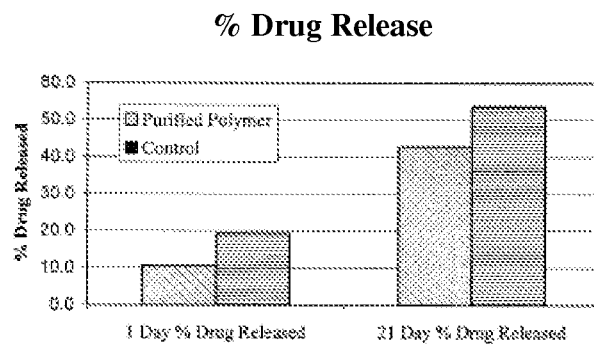
Figure 2. Octreotide Release as a Function of Polymer Type
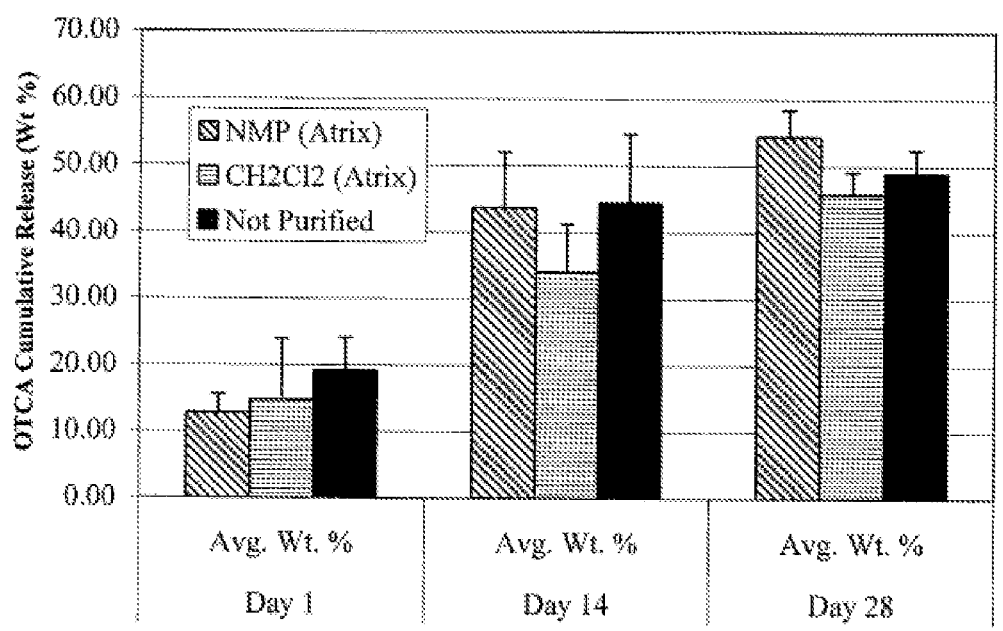

LOW-BURST POLYMERS AND METHODS TO PRODUCE POLYMER

CROSS-REFERENCE TO RELATED APPLICATIONS

This application is a divisional of U.S. application Ser. No. 12/527,377, filed Jun. 10, 2010, which is a nationalization under 35 U.S.C. 371 of PCT/US2008/001887, filed Feb. 13, 2008 and published as WO 2008/100532 A1 on Aug. 21, 2008, which claims the priority of provisional application U.S. Ser. No. 60/901,435, filed Feb. 15, 2007, which applications and publication are incorporated herein by reference and made a part hereof.

FIELD OF THE INVENTION

The field of the invention is improved lactide/glycolide copolymers for controlled release in vivo of bioactive substances, wherein the initial burst effect is reduced.

BACKGROUND

Compositions adapted for use in controlled release delivery systems, such as biodegradable and bioerodible implants, are known. See, for example, U.S. Pat. Nos. 7,019,106; 6,565,874; 6,528,080; RE37,950; 6,461,631; 6,395,293; 6,355,657; 6,261,583; 6,143,314; 5,990,194; 5,945,115; 5,792,469; 5,780,044; 5,759,563; 5,744,153; 5,739,176; 5,736,152; 5,733,950; 5,702,716; 5,681,873; 5,599,552; 5,487,897; 5,340,849; 5,324,519; 5,278,202; and 5,278,201. Such controlled release systems are in general advantageous as they provide for the controlled and sustained release of medications, often directly at or near the desired site of action, over the period of days, weeks or even months. Controlled release systems include polymer matrices that are known to be broken down in the body by various endogenous substances such as enzymes and water, such as polyesters including poly-lactide, poly-glycolide, and copolymers thereof ("PLG copolymers") prepared from glycolide (1,4-dioxan-2,5-dione, glycolic acid cyclic dimer lactone) and lactide (3,6-dimethyl-1,4-dioxan-2,5-dione, lactic acid cyclic dimer lactone). These copolymer materials are particularly favored for this application due to their facile breakdown in vivo by water or enzymes in the body to non-toxic materials, and their favorable properties in temporally controlling the release of biologically active agents ("bioactive agents") that may be contained within a mass of the polymer.

The release of many bioactive agents such as peptides, proteins, and small molecule drugs from controlled release systems can occur at a higher than optimal rate during the first 24 hours after implantation under certain conditions. This is known in the art as the "burst effect" or the "initial burst effect," and is potentially undesirable, as overdosing can result.

U.S. Pat. No. 4,728,721 discusses the presence of water-soluble unreacted monomers and water-soluble low molecular weight oligomers within the copolymers that are used to form microcapsules into which bioactive agents are incorporated. According to the inventors therein, the presence of these impurities tends to increase the initial burst effect, although the mechanism by which this burst occurs is undefined. The patent provides methods for removal of some of these impurities by washing of a solid form of the polymer with water, or by dissolving the polymer in a water-soluble organic solvent and adding the solution to water. The patent states that the ratio between the water and the polymer being purified is not critical, but that water should be used in large excess. Removal is effected exclusively of water-soluble materials such as lactic acid, glycolic acid, and very low molecular weight oligomers by this method.

U.S. Pat. No. 5,585,460 discusses the processing of polymers used for the preparation of microcapsules, wherein polymers produced without use of a catalyst are dissolved in a water-soluble organic solvent and precipitated in water, to provide polymers that are stated to have components with molecular weights under 1,000 (1 kD) of less than about 3%. In the '460 patent, the inventors therein state that the process claimed in the U.S. Pat. No. 4,728,721, discussed above, produces a polymer that, while it does reduce the amount of the initial release, also reduces the rate of release in later stages, whereas the method of the '460 patent allows for suppression of the initial burst while providing an increased rate of release at a later point in time.

U.S. Pat. No. 4,810,775 describes a process for purifying partly crystalline or amorphous polymers wherein high shear forces are applied at the time of contacting the polymer with a precipitating agent such as water so that minute particles of the polymer are obtained. This patent describes that such treatment results in the removal of residual monomers and catalysts from the polymer.

U.S. Pat. No. 7,019,106 discusses a process for producing a lactic acid polymer of 15,000 to 50,000 in weight-average molecular weight, the content of polymeric materials having not more than about 5,000 in weight-average molecular weight therein being not more than about 5% by weight. The process is characterized by hydrolysis of a high molecular weight lactic acid polymer and precipitation of the hydrolyzed product, which is stated to provide for a reduced burst effect. Desirable sustained release properties are attributed in part to a relatively high acid content per gram of copolymer.

However, despite these attempts to reduce the burst effect in controlled release compositions, there remains a need for compositions wherein the initial burst effect is reduced or minimized. This need is especially strong in the field of flowable compositions and injectable masses of controlled release compositions, as opposed to microcapsules, wherein physically larger masses of the polymer than are found in microcapsules are implanted in body tissue to provide for sustainable controlled release over longer periods of time.

SUMMARY OF THE INVENTION

The copolymers of the present invention when used in, for example, the controlled delivery systems known as liquid delivery systems, otherwise known as flowable delivery systems, like the Atrigel® systems that are disclosed in U.S. Pat. Nos. 6,565,874, 6,528,080, 6,461,631, 6,395,293, and references found therein, provide for substantially improved release rates for a bioactive agent, both a reduced initial burst and a desirable long-term sustained rate of release.

Unexpectedly, it has been discovered that use of these copolymer materials in the flowable delivery system effectively reduces the initial burst effect in the release of bioactive agents from the controlled release formulation after its implantation within living tissue, without loss of desirable long-term sustained rates of release of bioactive agents, particularly for those systems adapted to release a bioactive agent over a relatively prolonged period, such as 30 days to 6 months.

The present invention provides a biocompatible, biodegradable PLG low-burst copolymer material, termed a PLGp or a PLG(p) copolymer, adapted for use in a controlled release formulation, the low-burst copolymer material being characterized by a weight average molecular weight of about 10 kilodaltons to about 50 kilodaltons and a polydispersity index of about 1.4-2.0, and being further characterized by having separated therefrom a copolymer fraction characterized by a weight average molecular weight of about 4 kDa to about 10 kDa and a polydispersity index of about 1.4 to 2.5 (hereinafter the "removed copolymer fraction"). The inventive PLG low-burst copolymer material is prepared from a starting PLG copolymer material without a step of hydrolysis of a higher molecular weight PLG copolymer material, by dissolving the starting copolymer material, which is not a product of hydrolysis of a higher molecular weight PLG copolymer material, in a solvent, then precipitating the inventive low-burst copolymer material with a non-solvent. This process, as applied to a starting material that has never been subjected to hydrolysis, separates out an amount of the removed copolymer fraction effective to confer desirable controlled release properties including low initial burst upon the copolymer of the invention.

The starting PLG copolymer material can be prepared by any suitable means, including ring-opening polymerization of cyclic dimeric esters lactide and glycolide and condensation of lactic and glycolic acids. Preferably, the ring-opening polymerization of lactide and glycolide is used to prepare the starting copolymer from which the low-burst PLG copolymer of the invention is prepared. The ring-opening polymerization reaction, which can be a catalyzed reaction, for example using a tin salt such as stannous octanoate as a catalyst, incorporates two lactate or two glycolate units at a time as the polymerization progresses.

It is well known that a weight average molecular weight of a polymer material or fraction of a polymer material describes an average property derived from the individual molecular weights of all the individual polymer molecules making up the material or fraction. For any given weight average molecular weight that a polymer material or fraction may have there are many possible distributions of individual molecular weights of the molecules making up the material or fraction. Thus, in the present invention, the removed copolymer fraction having a weight average molecular weight of about 4 kDa to 10 kDa can include copolymer molecules with individual molecular weights ranging from a few hundred (oligomers) up to well in excess of 10 kDa. There are many different combinations of individual molecular weights that can yield any given value of the weight average molecular weight of a polymer sample. The breadth of the distribution of the individual molecular weights of the copolymer molecules making up the removed copolymer fraction of the invention is at least partially expressed by the polydispersity index, which can range from about 1.4 to about 2.5. Whatever the distribution of individual molecular weights may be in the removed copolymer fraction, the mass of the removed copolymer fraction amounts to about 2-20% of the sum of the masses of the removed copolymer fraction and the PLG low-burst copolymer material obtained thereby, more preferably about 3-15% of the sum of the masses, and yet more preferably about 5-10% of the sum of the masses. Typically, the greater the weight average molecular weight of the removed copolymer fraction within the defined range of about 4 kDa to 10 kDa, the greater is the weight average molecular weight of the inventive PLG low-burst copolymer material within the range of about 10 kDa to about 50 kDa.

The present invention provides a PLG low-burst copolymer material composed of a set of individual PLG copolymer molecular chains. A predominant proportion of these molecular chains predominantly include lactide/lactate residues adjacent to at least one end of each copolymer molecular chain and predominantly include glycolide/glycolate resides in internal domains of each copolymer molecular chain. It is believed that this distribution of lactide/lactate versus glycolide/glycolate units in the inventive copolymers may be responsible for their unexpected low burst and desirable sustained release properties.

The present invention further provides a method of preparation of a PLG low-burst copolymer material, wherein a removed copolymer material is separated from a starting PLG copolymer material by a step of dissolving the starting copolymer material in a solvent and precipitating the low-burst copolymer material by admixture of a non-solvent, without any step of hydrolysis of a higher molecular weight PLG copolymer being used in the process. The method of the present invention requires avoidance of a step of hydrolysis of a higher molecular weight copolymer material in order to provide a low-burst copolymer material of the invention. The inventive low-burst copolymer material exhibits surprisingly low initial burst properties as well as a surprisingly high sustained release effect. It is believed that this unexpectedly favorable low-burst property arises from the differing distributions of the more lipophilic lactate/lactide units adjacent to at least one end of the polymer chains in the present inventive polymer versus a polymer prepared with a step of hydrolysis. Copolymers prepared by a method including a step of hydrolysis can have a greater predominance of polymer chains that have the less lipophilic glycolate or glycolide units adjacent to both the molecular chain ends due to the hydrolysis of ester bonds in glycolate/glycolide rich internal domains.

In a low-burst PLG copolymer material prepared from a starting PLG copolymer that was made without using a core initiator, i.e., a PLG copolymer having a carboxyl group at one end of each chain and a hydroxyl group at the other end, the acid content per gram is lower in an inventive polymer than in a PLG copolymer prepared by a method including a step of hydrolysis of a higher molecular weight polymer, but the low-burst property of the inventive polymer is surprisingly at least as good as or better than that of the polymer prepared with a step of hydrolysis.

The relatively low acid content of the low-burst copolymers of the invention can be advantageous because the inventive copolymer material suffers from less acid-catalyzed auto-hydrolysis over time. If the starting PLG copolymer material comprises a PLGH, or acid terminated copolymer, the inventive process decreases the acid content per unit mass by removal of oligomers. The implication of a lower auto-hydrolysis rate of the polymer is that, for example, when implanted in the tissue of a patient, this lessening of auto-hydrolysis of the inventive copolymer enables a smooth monotonic, long lasting release profile of the bio active agent contained in a controlled release formulation, the copolymer also possessing a low initial burst.

BRIEF DESCRIPTION OF THE DRAWINGS

FIG. 1 shows the results of a study of the percentage release of octreotide from inventive copolymers versus control copolymers as a function of time.

FIG. 2 shows the degree of octreotide release from a controlled release formulation as a function of polymer type.

DETAILED DESCRIPTION OF THE INVENTION

Definitions of the Invention

In the present application, the terms "burst effect" or "initial burst effect" are used to refer to the burst effects in which a higher than optimal rate of diffusion of a bioactive agent out of a controlled release formulation occurs during the solidification of a liquid delivery system and/or during the initial period following implantation of a preformed solid implant such as a monolithic or a microparticulate implant. It is believed that the copolymers according to the present invention are particularly suitable for controlling this initial burst.

A "liquid delivery system" or a "flowable delivery system" is a combination of polymer, bioactive agent and organic solvent, such as in the Atrigel® system. Upon injection of the flowable material into tissue, the solvent disperses into the tissue and body fluid diffuses into the injected bolus, thereby causing coagulation of the polymer into a solid or semi-solid mass. Often, dispersion of the solvent out of the mass will carry the bioactive agent with it into surrounding tissues, thereby producing a burst effect. Solvents that can be used with the inventive polymers for a liquid or flowable delivery system include N-methylpyrrolidone, N,N-dimethylformamide, N,N-dimethylacetamide, dimethylsulfoxide, polyethylene glycol 200, polyethylene glycol 300, or methoxypolyethylene glycol 350.

A solid implant, of the monolithic or of the microparticulate type, also displays a burst effect due to the presence of bioactive agent on and near the surface of the implant, and due to the presence of easily leached bioactive agent within the micro-channels and mesopores that form within the implant as a result of its initial interaction with body fluid.

The term "low-burst" as used herein, such as a "low-burst copolymer material," refers to a phenomenon wherein this burst effect is minimized or reduced relative to that observed from a comparable art copolymer composition, while maintaining a desirable long-term release profile.

The terms "polymer" or "copolymer" as used herein refer to substantially linear polyesters, also referred to herein as "PLG copolymers," predominantly formed of monomeric lactate and glycolate hydroxyacids, or lactide and glycolide dimeric hydroxyacids, and include compositions referred to in the art as poly(lactate-glycolate), poly(lactate(co)glycolate), poly(lactide-glycolide), poly(lactide (co)glycolide), PLG, PLGH, and the like, with the understanding that additional moieties may be included, such as core/initiator groups (for example, diols, hydroxyacids, and the like), capping groups (for example, esters of terminal carboxyl groups, and the like) and other pendant groups or chain extension groups covalently linked to or within a polyester backbone, including groups that cross-link the substantially linear polyester molecular chains, without departing from the meaning assigned herein. PLG copolymers, as the term is used herein, includes molecular chains with terminal hydroxyl groups, terminal carboxyl groups (i.e., acid-terminated, sometimes termed PLGH) and terminal ester groups (i.e., capped).

As used herein, the term "polymer material" or "copolymer material" refers to the physical assembly or the combined mass of a plurality of individual polymer or copolymer molecules (molecular chains) in a given sample, respectively, each of which molecules (molecular chains) has its own defined molecular weight in the usual chemical sense of the word. A "polymer material" or "copolymer material" as used herein usually is composed of a set of individual polymer or copolymer molecules having various different individual molecular weights. Thus, when the molecular weight of such a polymer material or a copolymer material is referred to, it is an average molecular weight. Without further characterization, such an average molecular weight is a weight average molecular weight as used herein. The full description, weight average molecular weight, may be used synonymously. If the average molecular weight being referred to is the number-average molecular weight, it will be explicitly stated in this specification. When the individual molecular weights of the component individual molecules (molecular chains) is referred to, the term "individual molecular weight" is used in this specification. Weight average molecular weights are determined by the use of gel permeation chromatography (GPC) with reference to polystyrene standards, as is well known in the art.

The term "polydispersity index" as used herein is defined as the weight-average molecular weight of a sample of a polymer material divided by the number-average molecular weight of the sample of the polymer material. The definitions of the terms "weight-average molecular weight" and "number-average molecular weight" are well-known to those of skill in the art. The polydispersity index is well-known to characterize the distribution of molecular weights in a polymer. The higher the value of the polydispersity index, the broader the spread of individual molecular weights of the polymer molecular chains making up the polymer material. The lower the value of the polydispersity index, the more uniform and tightly grouped are the individual molecular weights of the individual polymer molecules making up the polymer material in question. In the unlikely event that every polymer molecule in the polymer material were identical, the weight-average molecular weight and the number-average molecular weight would be identical, and thus the polydispersity index ("PDI") would be unity.

The terms "lactate" and "glycolate" as used herein, depending upon context, refer to either the hydroxyacids, lactic acid and glycolic acid respectively, or their salts (lactates and glycolates) which are used as reagents in preparation of inventive copolymers, or refer to those moieties as residues incorporated via ester bonds into the inventive polyester molecular chains. When a copolymer is formed by polymerization of lactic acid (lactate) and glycolic acid (glycolate), each molecular chain consists of individual lactate and glycolate monomeric units incorporated into the copolymer molecular chain. The terms "lactide" and "glycolide" as used herein, depending upon context, refer to either the cyclic dimeric esters of lactate and glycolate respectively when referring to reagents used in preparation of inventive copolymers, or refer to those segments as incorporated ring-opened dimers in the formed polymer molecular chains. Thus, a statement about polymerization of lactide and glycolide refers to a polymerization reaction of the cyclic dimeric esters, whereas a statement about a lactide or glycolide residue within a copolymer molecular chain refers to that grouping of atoms, ring-opened, and incorporated into the copolymer chain. When a copolymer is formed by polymerization of lactide and glycolide, each incorporated lactide or glycolide residue is believed to consist of a pair of lactate or glycolate monomeric units, respectively. It is understood that when a lactide and glycolide residue in a copolymer molecular chain is referred to, the terms mean double (dimeric) units of two lactate (L-L), or two glycolate (G-G), residues in the molecular chain, respectively, such as is believed to result from the polymerization of lactide and glycolide.

When a lactate (L) or a glycolate (G) residue in a copolymer molecular chain is referred to, the terms mean single lactate (L) or glycolate (G) residues in the molecular chain, respectively, which can be within a lactide (L-L) or a glycolide (G-G) residue if the given lactate or glycolate is adjacent to another lactate or glycolate residue, respectively, regardless of the method used to prepare the copolymer molecular chain. As is most polymeric systems, this arrangement of residues is not all or none. Instead, the arrangement is a predominance. Thus, for the lactide and glycolide copolymers, a predominance of L-L and G-G residues will be present with some L and G (single) residues also present. The chemical reason underlying this characterization is the polymerization process. During polymerization, growing polymer chains are broken and reformed. This scission may split dimer residues and recombine single residues. For the lactate and glycolate copolymers, a predominance of L and G (single) residues will be present. This kind of polymer will have a relatively few sequences including repeats of dimer residues because of entropy factors.

It is understood that when the terms "lactic acid," "lactate," or "lactide" are used herein, that any and all chiral forms of the compounds are included within the terms. Thus, "lactic acid" includes D-lactic acid, L-lactic acid, DL-lactic acid, or any combination thereof; "lactide" includes DD-lactide, DL-lactide, LD-lactide, LL-lactide, or any combination thereof.

A substantially linear molecular chain as is formed by a polymerization process, such as a copolymer molecule that is within a copolymer material of the invention, has two ends, each end with a nearby "end domain," and an "internal domain" between the end domains. The terms are not exact, but rather describe general regions of a copolymer molecular chain, each end domain being the approximately 10-20% of the total length of the chain terminating at each of the two chain ends, and the internal domain being the remaining approximately 60-80% of the chain that lies between the end domains.

A "solvent" is a liquid, usually organic, that serves to dissolve a copolymer material to provide a homogeneous solution of the copolymer material. The term "non-solvent" refers to a precipitation solvent, that is a usually organic liquid, that is not a solvent for the copolymer. It is in this context that the term "non-solvent" is used herein. Two liquids, such as a solvent and a non-solvent, are "miscible" when they combine with each other in all proportions without phase separation. Solvents may be "soluble" in each other but not "miscible" when they can combine without phase separation in some, but not in all, relative proportions.

The preparation of an inventive low-burst copolymer material is carried out "without a step of hydrolysis of a higher molecular weight PLG copolymer material." By this is meant that, following the initial copolymerization of the monomers lactate and glycolate, or lactide and glycolide, to prepare a starting material for preparation of the inventive low-burst copolymer material, no conditions are applied, such as treatment with acid or alkali, that would hydrolyze ester bonds between adjacent monomeric units in the polymer. Therefore, a "higher molecular weight PLG copolymer material" as the term is used herein refers to a PLG copolymer material of a weight-average molecular weight that is greater than the weight average molecular weight possessed by a combination of the PLG low-burst copolymer material of the invention plus the removed copolymer fraction, such as exists in the starting PLG copolymer material prior to the step of separation of the removed copolymer fraction from the PLG low-burst copolymer material. This kind of hydrolysis does not refer to complete hydrolysis of a PLG copolymer back to its constituent monomers (lactate and glycolate), but rather to a step of partial hydrolysis whereby longer molecular chains are cleaved to yield shorter molecular chains, as is the case with certain art polymers adapted for use in controlled release formulations. Therefore, following the polymerization reaction, of whatever type it may be, that provides the starting PLG copolymer material, no step of hydrolysis is interposed prior to the separation of the removed copolymer fraction from the PLG low-burst copolymer material in the method of the invention, and the product of the invention has therefore not been subjected to a hydrolysis step. As discussed below, this absence of hydrolysis has implications for the distributions of lactide/lactate versus glycolide/glycolate units at the end domains of and in the internal domains of the molecular chains making up the inventive PLG low-burst copolymer material. As discussed above, PLG copolymer chains are enriched in G residues near the site of initiation of the polymerization reaction, and enriched in L residues in the regions incorporated late in the polymerization reaction. This implies that in PLG copolymer materials synthesized using, for example, a diol core from which polymerization proceeds in both directions, the internal domains of the polymer molecule near the core will be G-rich and both ends will be L-rich. In contrast, a PLG copolymer material of the PLGH type, which is polymerized from a lactic acid initiator, wherein polymerization takes place only at the hydroxyl end of the lactic acid, will be G-rich at the end of the molecular chain adjacent to the initiating lactic acid and L-rich at the distal end of the chain that is formed late in the polymerization reaction.

The term "acid content per unit mass" when used herein refers to the content of carboxylic acids, which are titratable using standard procedures well known in the art, divided by a unit mass such as 1 gram. PLG copolymers, being chains of hydroxyacids joined by ester bonds, typically have a single titratable carboxylic acid group at one end of the molecular chain. Thus, a sample of a copolymer made up of short molecular chains has a higher acid content per unit mass relative to a sample of a copolymer made up, on average, of longer (higher molecular weight) molecular chains. The sample made up of shorter, lower molecular weight chains has relatively more individual polymer chains and thus relatively more carboxylic acid groups per gram.

The inventive copolymer material is also known as a "PLGp" or a "PLG(p)" copolymer, the subscript "p" referring to "purified."

DETAILED DESCRIPTION OF THE INVENTION

The low-burst copolymer materials of the present invention are particularly useful in reducing the initial burst effect in controlled release formulations such as those of the Atrigel® type. The inventive copolymer material ("low-burst copolymer material") is characterized as being a derived from a sample of a PLG starting copolymer ("starting copolymer material"). The low-burst copolymer material is prepared without the use of a step of hydrolysis of a high molecular weight PLG copolymer. The inventive low-burst copolymer material is characterized by a weight average molecular weight of about 10 kilodaltons (kDa) to about 50 kDa and a polydispersity index of about 1.4-2.0. The low-burst copolymer material is obtained from a starting PLG copolymer material that is prepared by any suitable polymerization method but not including a step of hydrolysis in its preparation, from which a copolymer fraction ("removed copolymer fraction") that is characterized by a weight average molecular weight of about 4 kDa to about 10 kDa and a polydispersity index of about 1.4 to 2.5, has been removed.

The inventive copolymer material from which the removed copolymer fraction has been separated is prepared by purification from a PLG starting copolymer material. The PLG starting copolymer material is not a reaction product resulting from hydrolysis of a high molecular weight polymer, but otherwise can be made according to any of the standard methods well-known in the art, such as condensation polymerization of a mixture of lactate and glycolate, or ring-opening polymerization of a mixture of lactide and glycolide. Preferably, the ring-opening polymerization of lactide and glycolide is used to prepare the starting copolymer from which the low-burst PLG copolymer of the invention is prepared. The ring-opening polymerization reaction, which can be a catalyzed reaction, for example using a tin salt such as stannous octanoate as a catalyst, incorporates two lactate or two glycolate units at a time as the polymerization progresses In the inventive process, the removed copolymer fraction is separated from the starting copolymer material by dissolving the starting copolymer material in a solvent, then by adding a non-solvent to precipitate the low-burst polymer, and then collecting the inventive low-burst copolymer material, leaving the removed copolymer fraction in the supernatant.

The separation of the removed copolymer fraction that is characterized by a weight average molecular weight of about 4 kD to about 10 kD and a polydispersity index of about 1.4 to 2.5, to yield the low-burst copolymer material may be accomplished by methods according to the present invention. The separation is carried out by dissolution of the starting copolymer material in a solvent and precipitation of the low-burst copolymer material by mixture of this solution with a non-solvent. The solvent and non-solvent can be miscible. Specifically, the polymer can be dissolved in dichloromethane and precipitated with methanol.

In one embodiment according to the present invention, the low-burst copolymer material can have a weight average molecular weight of about 15 kDa to about 50 kDa, and a polydispersity index of about 1.4-1.8. Compared to the starting copolymer material from which the removed copolymer material has been separated, not only are the weight-average and the number-average molecular weights of the low-burst copolymer material somewhat greater, but even more significantly, the width of the spread of the individual molecular weights of the copolymer molecules is less, i.e., the molecular weight distribution is narrower. This narrowness is reflected in the relatively low polydispersity index of the low-burst copolymer according to the present invention.

When an inventive low-burst copolymer material was formulated as part of a controlled release system, such as the Atrigel® system, it was surprisingly found that a reduction of the initial burst effect in the release of a variety of peptide or protein bioactive agents was observed. This reduction was demonstrated by measurement of the amount of bioactive agent released from the controlled release system as a function of time. The low-burst copolymer material of the present invention, which is adapted to be used in the Atrigel® system, inter alia, was compared to the same formulation containing a polymer that was not purified by the inventive method. The formulation containing the low-burst copolymer material of the invention displayed a lower drug release in the first 24 hours and later time points. Thus, use of the low-burst copolymer in the Atrigel® system demonstrates a simple, effective process to improve in vivo drug release kinetics, especially with respect to drug release during the first 24 hours after administration.

The starting copolymer material can be prepared by any means known in the art, such as: polymerization of a mixture of the cyclic dimer esters, lactide and glycolide, for example with a catalyst such as stannous octanoate, with or without a core/initiator such as lactic acid or a diol; polymerization of a mixture of lactic acid and glycolic acid, for example with an acid catalyst, under dehydrating conditions; or any other suitable method. The starting copolymer material is not subjected to a step of hydrolysis prior to the steps of separation. This non-hydrolysis factor is believed to be significant in providing the unexpected low-burst properties of the inventive copolymer materials.

It is well known in the art that in the polymerization of lactide and glycolide in the presence of a catalyst, a suitable means for preparing the starting copolymer material of the invention, the glycolide molecules react in the ring-opening polymerization reaction at a higher rate than do the lactide molecules, due to the lesser steric hindrance of glycolide relative to lactide (lactic acid bearing a methyl group in place of a hydrogen atom of glycolic acid). This results in the early-polymerizing regions of the growing copolymer chain predominantly deriving from glycolide incorporation. As the glycolide concentration in the reaction mixture drops during the course of the polymerization process due to this selective depletion of monomer, the late-polymerizing regions of the copolymer chain predominantly are derived from lactide incorporation. Thus, as polymerization occurs in both directions, the internal regions or internal domains of the molecular chains are composed predominantly of glycolide residues, and the ends of the chains are composed predominantly of lactide residues. By "predominantly" is meant herein that the one component, lactide or glycolide, is found more frequently than the other component; i.e., a predominantly glycolide-incorporating or glycolide-containing domain or region of a copolymer chain has more glycolide residues than lactide residues in the domain on a molar basis as defined relative to the molar concentrations of the monomers in the starting reaction mixture; or, in other words, glycolide is over-represented in that region or domain of the polymer relative to its initial proportion in the polymerization reaction mixture. In a predominantly glycolide- or glycolate-containing domain, glycolide/glycolate residues are found at a higher molar percentage in that domain than they represent in the starting reaction mixture, and lactide/lactate residues are found at a lower molar percentage in the domain than they represent in the starting reaction mixture.

The difference in distribution of lactide/lactate vs. glycolide/glycolate moieties along the polymer chain will vary from slight to significant depending upon the reaction time allowed for post polymerization rearrangement. This post-polymerization period is balanced against increasing weight average molecular weight of the copolymer material. Accordingly, within the weight average molecular weight parameters of this invention, the difference in distribution will be moderate to significant, preferably in the range of 5 to 35%, more preferably 10-25%, on a molar basis.

Thus, the molecular chains making up a low-burst copolymer material of the invention, as a result of the method of preparation either from lactate/glycolate or from lactide/glycolide without a step of hydrolysis following polymerization, are believed to have predominantly lactide/lactate residues in the end domains of the molecular chains and glycolide/glycolate residues in the internal domains of the molecular chains. It is well-known in the art that lactide/lactate residues have a higher degree of hydrophobicity than do glycolide/glycolate residues, as a result of the presence in lactide/lactate residues of a hydrophobic methyl group. Based on this fact, it is believed that a low-burst copolymer material of the invention can present a more hydrophobic domain to its surroundings, as the ends of the chains are likely more accessible to other molecules in the surrounding environment. This enhanced hydrophobicity of the chain end domains may be a cause of the unexpected low-burst properties of the inventive copolymers. While not wishing to be bound by theory, it is believed that this degree of hydrophobicity may cause, at least in part, the unexpected but desirable low-burst properties of an inventive polymer relative to art polymers due to its hydrophobic interactions with the contained bioactive agent and resulting changes in the partition coefficients of the bioactive agent between the copolymer matrix and the surrounding solutions of body fluids when implanted in a patient.

An art copolymer, such as can be prepared by hydrolysis of a high molecular weight precursor copolymer, is believed to differ from an inventive polymer in that the molecular chains making up the art copolymer material do not have predominantly lactide/lactate containing domains at both ends of the molecular chains. This difference is the result of hydrolysis of a high molecular weight precursor. Upon hydrolysis of a high molecular weight precursor polymer, the resulting cleavage causes one end (the newly formed end) to contain predominantly glycolide/glycolate residues rather than lactide/lactate residues. This effect occurs to a great extent within the interior domain on a purely statistical basis, and is further enhanced by the well-known fact of the reduction of the rate of ester hydrolysis reactions due to steric hinderance. Thus, less hindered ester bonds (such as glycolate bonds as opposed to lactate bonds) are expected to hydrolyze at a higher rate under given conditions than are more hindered ester bonds. As a result, hydrolysis of the ester bond between adjacent glycolate residues (G-G) is believed to take place more readily, at a higher rate, than hydrolysis of the ester bond between a lactate and a glycolate residue (L-G or G-L) which is likewise believed to take place more readily, at a higher rate, than hydrolysis of the ester bond between to lactate residues (L-L). As a consequence, in a copolymer chain that consists of all three types (G-G, G-L/L-G, and L-L) of ester bonds, an ester bond would be more frequently cleaved at the G-G ester linkages than at any of the other types of ester linkages, with L-L ester linkages occurring least often at the lowest relative rate. Thus, a G-G rich domain such as the internal domain of the copolymer will more frequently be the site of hydrolysis than any other domain. Therefore, a copolymer molecular chain that has undergone hydrolysis will yield, as a reaction product copolymer, molecular chains that will tend to have at least one end of the product chain or possibly both ends of a product chain formed predominantly of glycolide/glycolate residues, rather than being formed predominantly of lactide/lactate residues as in the inventive copolymers.

As a result, copolymer materials that have been prepared by a method including a step of hydrolysis of a high molecular weight copolymer chain will be made up of copolymer molecular chains that have more ends formed predominantly of glycolide/glycolate residues than of lactide/lactate residues. This would be expected to result in a less hydrophobic environment that the end regions of these copolymer molecular chains present to the surrounding environment, and may account for the less desirable high initial burst properties of art copolymers prepared by the hydrolysis method compared to the more desirable low initial burst properties of inventive copolymers as disclosed and claimed herein.

As a consequence of the above-discussed rate of incorporation and rate of hydrolysis factors, the removed copolymer material of the present invention is also different than copolymer fractions that may be removed in art processes using solvent/non-solvent precipitation techniques. The art copolymer for use in controlled-release formulations that has been prepared by a method including hydrolysis of a high molecular weight copolymer, following by dissolution in a solvent and precipitation of a fraction of the hydrolyzed copolymer with a non-solvent, will not only have different distributions of lactide/lactate (L) and glycolide/glycolate (G) in the precipitated fraction, but the art non-precipitated material will also have different distributions of L and G along the molecular chains compared to the non-precipitated fraction of the present invention. The non-precipitated, typically lower molecular weight, copolymers resulting from a process involving hydrolysis would likewise be expected to have a higher proportion of G residues at or near the chain termini than copolymers that had not undergone a hydrolysis step. Furthermore, due to the unexpectedly good low-burst properties of the inventive polymers, the acid content of a copolymer used in a controlled release formulation such as an Atrigel® system can be reduced yet still achieving a comparable decrease in the undesired burst effect. It is well known in the art that a higher acid content per unit mass can diminish the undesired burst effect, and art copolymers used in this application have been tailored to achieve this result. However, from another perspective a relatively higher acid content per unit mass is undesirable, in that the rate of auto-catalyzed hydrolysis of the PLG copolymer ester bonds would be greater due to the higher acid catalyst concentration in situ. Auto-hydrolysis of copolymer ester bonds is known to result in more rapid decomposition of the polymer, which would tend to interfere with achieving a desirable smooth, monotonic release of the bioactive ingredient formulated with the copolymer in a controlled release preparation such as Atrigel®.

Therefore, the inventive products by process can be clearly distinguished structurally over the products produced by a step of hydrolysis of high molecular weight copolymers.

The starting copolymer of the present invention can be prepared by any available method, not including a step of hydrolysis of a high molecular weight copolymer, but including ring-opening polymerization of mixtures of lactide and glycolide precursors, dehydrative polymerization of lactic acid and glycolic acid, and the like. Purification of the starting copolymer by a method of the invention is carried out by dissolving the starting copolymer material in a solvent, for example, dichloromethane or any other suitable organic liquid. Precipitation is carried out by contacting that solution with a non-solvent, for example either by adding the copolymer solution to a volume of a non-solvent, or by adding a volume of a non-solvent to the copolymer solution. An example of a typical non-solvent is methanol. Preferably, the solvent and the non-solvent liquids are miscible, or at least substantially soluble, in each other. The mixing of the copolymer solution and the non-solvent can take place under a wide variety of temperatures, concentrations, and modes of mixing.

A copolymer of the invention can be used to advantage in a number of differing types of controlled release formulations, each of which can embody a variety of different bioactive agents and used for the treatment of different malconditions. The low-burst property of the inventive polymers are particularly well-suited to use with bioactive agents wherein overdose and potential toxicity of the agent are of medical concern, as well as with bioactive agents with which it is medically indicated to maintain a relatively constant dosage over a prolonged period of time.

Examples of bioactive agents that can advantageously be used with controlled release formulations incorporating a copolymer of the invention include leuprolide and related peptide analogs useful for modulating LHRH levels; steroids such as can be used for birth control, treatment of cancers such as breast cancer, and the like; prostaglandins, such as latanoprost and travoprost that can be used for treatment of glaucoma; analgesics, such as oxycodone, for treatment of chronic pain; carbonic anhydrase inhibitors such as brinzolamide and dorzolamide, useful for treatment of glaucoma and hypertension; adrenergic antagonists such as brimonidine or betaxolol, useful as an anti-hypertensives; or any other bioactive agent for which sustained or controlled release is medically indicated. The inventive copolymers can be used in differing types of controlled release formulations.

A flowable delivery system such as in an Atrigel® system, comprising an inventive copolymer, a water-soluble organic solvent such as N-methylpyrrolidone, N,N-dimethylformamide, N,N-dimethylacetamide, dimethylsulfoxide, polyethylene glycol 200, polyethylene glycol 300, or methoxypolyethylene glycol 350, and a bioactive agent such as leuprolide, can be advantageously used in a patient to avoid or minimize the initial burst effect while providing for a prolonged period of sustained release of the bioactive agent. Likewise, both monolithic and microparticulate solid implants incorporating a bioactive agent that are preformed from an inventive copolymer offer similar benefits of low initial burst and prolonged sustained release of the bioactive agent. Other embodiments of sustained release systems and compositions will be apparent to those of skill in the art.

A flowable delivery system such as an Atrigel® system comprising an inventive PLG low-burst copolymer material can be used in the treatment of a variety of malconditions. The invention provides a method for the treatment of a malcondition using such a flowable delivery system. For example, a flowable delivery system of the invention can be used in the treatment of prostate cancer with leuprolide, a peptide drug used in the suppression of testosterone biosynthesis in men, a treatment that is often medically indicated for patients afflicted with prostate cancer. Implantation of a flowable composition subcutaneously results in the formation of a semi-solid depot as the organic solvent diffused into surrounding tissues and body fluid, as body fluid diffuses into the bolus. This semi-solid or solid depot then serves to release the leuprolide in a controlled or sustained manner over a prolonged period of time, which can be in the order of months. Use of the inventive copolymer materials is effective in reducing the undesirable initial burst effect that can result from the use of art copolymers in a similar system.

In a similar manner, other bioactive agents can be used in the treatment of other types of malconditions when it is medically indicated to provide the bioactive agent to the patient over the course of weeks or months. For example, a flowable delivery system incorporating octreotide can be used to form a depot for the treatment of acromegaly, the treatment of diarrhea and flushing episodes associated with carcinoid syndrome, and treatment of diarrhea in patients with vasoactive intestinal peptide-secreting tumors.

In the treatment of the malcondition of glaucoma, a flowable delivery system of the Atrigel® type incorporating an inventive PLG copolymer and comprising a bioactive agent suitable for the treatment of glaucoma, for example a prostaglandin analog such as latanoprost or travoprost or their free acid forms, a carbonic anhydrase inhibitor such as dorzolamide or brinzolamide, an α-adrenergic antagonist such as brimonidine, or a β-adrenergic antagonist such as betaxolol, can be advantageously used to deliver the bioactive agent over a prolonged period while avoid the initial burst effect. The flowable delivery system to be used to form a depot either intraocularly, through direct injection into the eyeball, or in proximity to the eye through implantation in a nearby tissue.

A flowable delivery system incorporating an inventive PLG low-burst copolymer and including terbinafine as a bioactive agent can be used for treatment of onychomycosis of the toenail or fingernail by formation of a depot underneath the nail.

A flowable delivery system incorporating an inventive PLG low-burst copolymer and including a steroid can be used to provide a birth control treatment, wherein a prolonged controlled release is desired to control unwanted fertility and to suppress ovulation while avoiding potential side-effects from steroid overdose that could occur due to initial burst when using an art copolymer for this application.

A flowable delivery system incorporating an inventive PLG low-burst copolymer and including an antibiotic, e.g., dapsone, can be used in the treatment of chronic infection.

A flowable delivery system incorporating an inventive PLG low-burst copolymer and including an antipsychotic, e.g., risperidone, can be used in the treatment of psychosis.

A flowable delivery system incorporating an inventive PLG low-burst copolymer and including rapamycin, an immunosuppressant, can be used in the treatment of cancer or in controlling tissue rejection as in tissue or organ transplantation.

A flowable delivery system incorporating an inventive PLG low-burst copolymer and including an antiviral agent, e.g., AZT, can be used in the treatment of a viral infection.

Other conditions and appropriate medicaments for their treatment will be apparent to those of skill in the art.

EXAMPLES

Certain examples are provided below in order to assist in understanding embodiments of the present invention; they should not, however, be considered as limiting the present invention, which are described in the claims.

Introduction to the Purification of Biodegradable Polymers to Improve In Vivo Release Kinetics.

The release of many active agents such as peptides and proteins from the Atrigel® system can occur at a higher than optimal rate during the first 24 hours after implantation under certain conditions. The polymers of the instant invention in combination with the Atrigel® systems results in a unique combination that provides substantially improved low-burst release rates.

The polymer used in the Atrigel® system is purified by dissolution in a solvent and precipitation in a non-solvent, then dried. The solvent and non-solvent can be miscible.

Specifically, the polymer can be dissolved in dichloromethane and precipitated into methanol. As described below, the formulation containing purified material was compared to the same formulation containing a polymer that was not purified by the inventive method. The formulation containing purified material displayed a lower drug release in the first 24 hours and later time points. Use of an inventive copolymer in the Atrigel® system is thus shown to improve in vivo drug release kinetics, especially with respect to drug release during the first 24 hours after administration.

Example 1

Purification of Acid Terminated 85/15 Poly(DL-Lactide-Co-Glycolide) (85/15 PLGH)

Test articles were prepared with and without the purified copolymer and compared with the starting copolymer (the copolymer prior to carrying out steps of dissolution and precipitation) in a 24 hour release study. The starting copolymer in this Example was an acid-terminated form of poly(DL-lactide-co-glycolide), meaning that one end of the molecular chains making up the copolymer material bear a carboxylic acid group. Forty-eight grams of 85/15 PLGH with an inherent viscosity of 0.25 dL/g was dissolved in 100 mL of dichloromethane. The polymer solution was poured into a 2 L beaker containing 500 mL of methanol with vigorous stirring. The precipitated polymer formed a soft mass. The dichloromethane-methanol solution was decanted and 200 mL of methanol was added for 5-15 minutes to further extract the dichloromethane. The methanol was decanted from the container and replaced with 100 mL of methanol for an additional 5-15 minutes to further extract the dichloromethane.

The polymer mass was removed from the container and placed in a Teflon-lined glass dish and dried under vacuum at 40° C. for 48 hours. The dried polymer was removed from the vacuum oven, ground into a powder and dried another 24 hours at 40° C.

Preparation of Atrigel® Formulations

Solutions (45% w/w) of both purified and unpurified copolymers in N-methylpyrrolidone (NMP) were prepared. Stock solutions were prepared by weighing a known amount of each copolymer into individual 20 mL scintillation vials. The appropriate amount of NMP was added to each polymer and the mixture placed in a jar mill. The vials were mixed at least overnight, producing a visually clear polymer solution. The polymer solutions were gamma-irradiated. The characterization data for the purified and unpurified polymer in solution is shown in Table 1.

TABLE 1

Characterization Data for Purified and Unpurified Polymer; Molecular weight and Polydispersity Data is for Post Gamma-Irradiated Polymer

| Sample | MW (kDa) | PDI [1] | Mole % DL-lactide in Polymer | Mole % Glycolide in Polymer | Wt % DL-lactide Monomer | Wt % Glycolide Monomer |
|---|---|---|---|---|---|---|
| Purified Polymer | 19 | 1.6 | 84.7 | 15.3 | 0.5 | 0.1 |
| Unpurified Polymer | 18 | 1.7 | 84.5 | 15.5 | 2.3 | 0.1 |

[1] Polydispersity Index = Weight Average Molecular Weight/Number Average Molecular Weight An octreotide acetate-citric acid mixture was prepared by dissolving 4 g of octreotide acetate, and 0.7550 g citric acid (1:1 mole:mole) into 30 mL HPLC grade water. The solution was stirred until all of the solids were in solution. The solution was divided into 5 separate vials, and was frozen at −86° C. for 1 hour. The vials were then lyophilized for 2 days.

A stock solution of drug was prepared by dissolving 1.35 g of drug in 4.65 g HPLC grade water, yielding a 22.5% (w/w) stock solution. Drug containing syringes ("B" or male syringes) were prepared by pipetting 500 mg of octreotide stock solution into 1.25 mL BD syringes, followed by lyophilization for 24 hours. Polymer solution containing syringes ("A" or female syringes) were prepared by weighing 637.5 mg polymer solution into 1 mL female syringes.

Prior to administration in rats, the two syringes were mated together and the contents mixed by forcing the contents of the syringes between chambers a predetermined number of times. Once the contents of the two syringes were mixed, a 19 gauge thin-wall needle was attached to the female syringe and approximately 100 mg of Atrigel® formulation injected subcutaneously into a rat.

At predetermined times, five rats per group were euthanized with carbon dioxide and the Atrigel® implants recovered. The implants were analyzed for the amount of drug remaining in the implant by HPLC and the % drug release was calculated.

The drug release from the purified polymer test article was compared to the test article with the same polymer without purification. The data, means and standard deviations are displayed in Table 2 and in FIG. 1.

TABLE 2

Mean % Drug Released After 24 Hours

| | Purified Polymer Day 1 % Release | Control Polymer Day 1 % Release | Purified Polymer Day 21 % Release | Control Polymer Day 21 % Release |
|---|---|---|---|---|
| | 11.64 | 20.70 | 43.3 | 51.6 |
| | 13.00 | 28.00 | 42 | 63.5 |
| | 8.60 | 16.20 | 50.6 | 52.7 |
| | 10.53 | 15.40 | 42.2 | 50.5 |
| | 8.70 | 15.70 | 35.8 | 49.7 |
| Mean | 10.49 | 19.20 | 42.78 | 53.60 |
| Std. Dev. | 1.90 | 5.37 | 5.27 | 5.65 |

Example 2

In Example 2, test depots comprising octreotide as a bioactive agent were prepared from polymers purified by two different methods and compared to a test article prepared from the same polymer in unpurified form, in a 28 day controlled release study in rats.

Example 2a

Purification of Polymer in NMP/Water/Ethanol (Control Method)

A purification technique was developed that involved dissolving the polymer in N-methyl pyrrolidone (NMP) and precipitating the polymer solution into a water/ethanol solution. NMP, water, and ethanol can have advantageous properties when used in pharmaceutical preparations compared to dichloromethane (methylene chloride) and methanol.

The polymer was dissolved in NMP for use in the delivery system. One hundred grams (100 g) of 85/15 PLGH was added to 400 g of NMP in a 2 L Nalgene bottle. The bottle was shaken to disperse the polymer and placed on a roll mill overnight to dissolve the polymer.

A 9.5 L container was equipped with an overhead stirrer set off-center and filled with 4 L of water. With the overhead stirrer at approximately 1250 rpm (Setting 3), the polymer solution was slowly added to the container through a funnel over a 5 minute time period. The resulting polymer suspension was stirred for 30 minutes at 1250 rpm. The stirring was then slowed to about 500 rpm while 3 L of water and 1 L of ethanol was added to the container. The polymer suspension aggregated and was redispersed by increasing the stir speed to approximately 800 rpm (setting 2.5) and manually breaking up the aggregate.

After 30 minutes the stirring was stopped and the suspension allowed to settle and separate for 20 minutes. A small amount of solids rose to the surface, but the majority of material settled to the bottom of the container. Four liters (4 L) of solvent were decanted from the container and stirring was resumed approximately 800 rpm while 3 L of water and 1 L of ethanol was added. Stirring was continued for 30 minutes and then the suspension was allowed to settle and separate for 30 minutes. Four liters (4 L) of solvent was then decanted from the container.

Stirring was resumed at the 800 rpm setting and 3 L of water and 1 L of ethanol again added and stirring continued for 2 hours. The mixture was allowed to settle for 15 minutes. Four liters (4 L) of water was added to the container and stirred for an additional 1-2 hours. The suspension was filtered and the filter cake was spread into a Teflon lined Pyrex dish and dried in a vacuum oven at room temperature for approximately 70 hours. The weight was recorded and placed back in the vacuum oven and dried under vacuum at 30-40° C. for an additional 19 hours. The dried powder was transferred to a glass jar.

Example 2b

Purification of Polymer in Dichloromethane/Methanol (Test Method)

One hundred grams (100 g) of 85/15 PLGH was added to 393 g of dichloromethane (DCM) in a 1 L Nalgene bottle. The bottle was shaken to disperse the polymer and placed on a roll mill overnight to dissolve the polymer.

A 9.5 L container was filled with 4 L of methanol. The polymer solution was slowly added to the methanol through a funnel in a thin stream without stirring. The polymer formed a soft mass in the bottom of the container. The material was manipulated with a stirring rod to expose fresh surface area to assist in DCM diffusion into the methanol.

After 15 minutes, the solution was decanted and 2 L of fresh methanol was added. The material was again manipulated to generate new surface area to allow the DCM to diffuse out of the polymer and into the methanol. The soft mass was periodically kneaded to press out solvent and force DCM into the methanol.

After about 5 hours the excess solvent was pressed out of the soft polymer mass and it was placed in a Teflon lined Pyrex dish, placed in a vacuum oven and solvent removed by vacuum at room temperature. After about 24 hours, the brittle material was ground to a powder and placed back in the vacuum oven to further dry. After 48 hours, the polymer was weighed and placed in the vacuum oven at 30-40° C. The polymer was weighed again after 19 hours and the weight had not changed significantly. The polymer was placed in Nalgene bottle. The final yield was 61 g.

Example 2c

Preparation of Bulk Atrigel® Formulations

Fifty percent (50%) polymer solutions in NMP were prepared by weighing both components into a 20 mL glass vial. The vial was placed on a roll mill to dissolve the polymer into the NMP. The following copolymer samples were prepared:

Polymer 2A: 5 g of (85/15 PLGH purified in NMP/Water/Ethanol) was dissolved in 5 g of NMP.
Polymer 2B: 5 g of (85/15 PLGH purified in DCM/methanol) was dissolved in 5 g of NMP.
Polymer 2C: 5 g of (85/15 PLGH unpurified) was dissolved in 5 g of NMP.

The bulk solutions were irradiated and filled into syringes. The bulk formulations were characterized by gel permeation chromatography to measure the molecular weight of the polymer in the solution after irradiation. Molecular weight data are given in Table 3.

TABLE 3

Characterization Data for Purified Polymers and Control Polymer after Gamma Irradiation

| Polymer | Purification Technique | Molecular Weight (kDa) (n = 2) | Polymer Dispersity Index (n = 2) |
|---|---|---|---|
| 2A | NMP/Water/EtOH | 21 | 1.8 |
| 2B | DCM/MeOH | 21 | 1.7 |
| 2C | Unpurified | 21 | 1.7 |

Example 2d

Preparation of Drug Loaded Syringes

OTCA (Octreotide acetate (2.33 g) and citric acid (0.43 g)) were dissolved in 21.24 g of water. The appropriate amount of solution was weighed into 5 CC syringes and frozen at −80° C. and lyophilized.

Example 2e

Preparation of Test Depots

Prior to administration in rats, the syringe containing the Atrigel® formulation was mated to the syringe containing the lyophilized drug and the contents were mixed by forcing the contents of the syringes between chambers a predetermined number of times. Once the contents of the two syringes were mixed, a 19 gauge thin-wall needle was attached to the female syringe and approximately 100 mg of Test Article injected subcutaneously into a rat.

750 mg of constituted product was prepared by mixing 112.5 mg drug in 637.5 mg of ATRIGEL® vehicle. The homogeneous mixture was then weighed into a 1.5 ml, syringe and a 19 gauge thin-wall needle was attached. Each rat receive approximately 100 mg of the constituted product via subcutaneous injection.

At predetermined times five rats per group were euthanized with carbon dioxide and the Atrigel® implants recovered. The implants were analyzed for the amount of drug remaining in the implant by HPLC and the cumulative percentage of drug released calculated. The data for the 1-, 14-, and 28-day time points are shown in Table 4 and FIG. 2.

TABLE 4

Release Data

| n = 5 | Day 1 Avg. Wt. % OTC Released | Day 1 STD Dev | Day 14 Avg. Wt. % OTC Released | Day 14 STD Dev | Day 28 Avg. Wt. % OTC Released | Day 28 STD Dev |
|---|---|---|---|---|---|---|
| NMP (Atrix) | 12.83 | 2.79 | 43.73 | 8.34 | 54.45 | 3.94 |
| $CH_2Cl_2$ (Atrix) | 14.75 | 9.22 | 34.09 | 7.16 | 45.91 | 3.25 |
| Not Purified | 19.16 | 4.94 | 44.46 | 10.28 | 48.93 | 3.57 |

The test articles prepared with both forms of purified polymers had initial lower burst that the test article using the unpurified polymer, the percent release of octreotide from the NMP and DCM copolymer preparations at Day 1 being the same within experimental error but significantly lower than from the unpurified polymer. However, at Days 14 and 28, the test depot containing a polymer purified by the DCM method indicated a significantly slower release of octreotide than did the depots formed from the NMP-purified polymer or from the unpurified polymer.

The molecular weight data in Tables 1 and 3 illustrate that the purification did not significantly alter the weight average molecular weights of the polymers in the gamma irradiated formulations. The purification did, however, narrow the molecular weight distribution or polydispersity index when compared to the control.

To further understand this phenomenon, an 85/15 PLGH polymer purchased from an outside vendor (referred to as unpurified polymer 2D) was purified in DCM and methanol using a method similar to that described above. This lot of purified polymer was labeled polymer 2E. The polymers were characterized by GPC and NMR. In addition, the impurities that remained in the DCM/methanol solvent were collected and characterized by GPC and NMR. The data appear in Table 5.

TABLE 5

Characterization Data for Raw and Purified 85/15 PLGH and Residue of Purification

| | | | Mole % of Monomer in Polymer | | Weight % Monomer | |
|---|---|---|---|---|---|---|
| Sample | MW (kDa) | PDI [1] | DL-lactide | Glycolide | DL-lactide | Glycolide |
| Unpurified polymer 2D | 23 | 1.73 | 84 | 16 | 1.7 | 0.1 |
| Purified Polymer 2E | 23 | 1.66 | 83 | 17 | 0.5 | 0 |
| Polymer Residue 2E | 4 | 1.5 | 83 | 17 | 1.4 | 0 |

[1] Polydispersity Dispersity Index = Weight Average Molecular Weight/ Number Average Molecular Weight The NMR data indicated that the purification removed residual monomer. The weight percent lactide was reduced from 1.7 wt % to 0.5 wt % and the residual glycolide monomer was reduced from 0.1 wt % to 0 wt %. The GPC data again shows that while the weight average molecular weight did not significantly change, the polymer dispersity index (PDI) decrease from 1.73 to 1.66, indicating removal of a low molecular fraction of the polymer. This low molecular weight fraction left in the solvent mixture had an average molecular weight of only 4 kDa.

Example 2f

Method of Analysis of Residual Octreotide in Recovered Implants

I. Implant Preparation
A. Implants are received from the Pre-clinical department in labeled 20 ml Scintillation vials
B. The implants are frozen at −86° C. for at least 1 hour
C. The implants are then lyophilized for 4 or more hours or until dry
D. Dried implants are then minced with scissors
II. Implant Extraction
A. An extraction solvent solution consisting of 70:30 DMSO:MeOH+1% PEI is prepared by measuring 700 ml of DMSO and 300 ml of MeOH in a graduated cylinder. The solvents are added to a 100 ml bottle. The bottle is shaken to mix the solvents. 10 g of PEI is weighed into a 250 ml beaker. The PEI is transferred to the solution by adding small amounts of the mixed solution to the PEI beaker and swirling, then adding the solution back to the solvent bottle. The process is continued until no PEI remains in the beaker.
B. 5.0 ml of extraction solvent is added to the minced implants using a micro-pipetter
C. The implant solution is placed in a horizontal shaker set of 37° C., 200 RPM. The samples are shaken overnight.
III. Extraction Solution Filtration and Dilution
A. 2 ml of implant extract is filtered using a 3 ml syringe and 0.2 um nylon syringe filter into a 10 ml test tube. 1 ml of the filtrate is aliquoted to second tube using a 1 ml micropipetter.
B. A dilution solvent consisting of 50:50 Acetonitrile:water is prepared by measuring 500 ml of Acetonitrile (ACN) in a graduated cylinder and adding the solvent to a 1000 ml bottle. 500 ml of water is added to the bottle and the bottle is shaken to mix the solvents.
C. 4.0 ml of dilution solvent is added to the aliquoted implant extract. The solution is vortex mixed until no phase separation is observed.

D. The diluted extract is filtered using a second 3 ml syringe and nylon syringe filter. The extract is filtered into a 2 ml HPLC vial and capped for HPLC analysis.

IV. HPLC Analysis

A. Standard Curve Preparation

A standard curve is prepared using the Octreotide drug powder (OTCA or ODP) used in the test articles for the study the implants are collected from. 10.00 mg of Octreotide drug powder is weighed into a 10 ml volumetric flask. The flask is brought to volume using Octreotide mobile phase (see section IV B, mobile phase preparation.). The flask is vortex mixed until all powder is in solution. The prepared stock solution is further diluted with mobile phase to prepare a standard curve using 1000 ml and 100 ml micropipetters. The dilutions are made into 2 ml HPLC vials. The dilution volumes are outlined below.

B. Mobile Phase Preparation

2 L of 65:35 PO4:ACN buffer (octreotide mobile phase) is prepared by weighing 14.047 g of $Na_2HPO_4*7H_2O$ into a weigh boat. The powder is added to a 2 L volumetric cylinder. 0.7839 g of $NaH_2PO_4$ is weighed into a weigh boat and added to the cylinder. HPLC grade $H_2O$ is added to the cylinder to the 1300 ml mark. A stir bar is added and the solution is stirred until all solids are dissolved. The pH of the buffer is adjusted to pH 7.4 using ortho phosphoric acid. Acetonitrile is the added to the flask to the 2000 ml mark. The mobile phase is stirred well ad degassed for 10 min using a sonicator bath.

C. HPLC Parameters:

The analytical column used is a Merck LiChroSphere 125×4 mm RP select B 5 um. After each run, two cleaning steps are run. The first is a 30 min run with 70:30 $H_2O$:ACN, the second is a 30 min run with 30:70 $H_2O$:ACN.

TABLE 6

Release of a peptide from an ATRIGEL ® delivery system*.

| | | Delivery System | | 24 Hour % Release Average (Standard Deviation) | |
|---|---|---|---|---|---|
| Study | Active | Solvent | Polymer | Purified Polymer | Unpurified Polymer |
| ATRS 963 | 0.16% PYY | 55% NMP | 45% 50/50 PLGH (IV 0.37) | 45.6 (9.9) | 57.6 (7.7) |
| QRS-R041-05 | 0.8% Leuprolide Acetate | 60% NMP | 40% 65/35 PLGH (0.37 IV) | 23.9 (6.8) | 56.5 (7.2) |
| QRS-R026-05 | 10% GHRP-1 (plus citric acid) | 50% NMP | 50% 85/15 PLGH (25 kDa) | 14.2 (8.6) | 27.9 (7.5) |
| ATRS-606 and QRS-R026-05 | 10% GHRP-1 (plus citric acid) | 50% NMP | 75/25 PLGH (IV 0.24) | 5.3 (1.7) | 22.4 (3.0) |

*copolymer purification was with dichloromethane/methanol.

While the invention has been described and exemplified in sufficient detail for those skilled in this art to make and use it, various alternatives, modifications, and improvements will be apparent to those skilled in the art without departing from the spirit and scope of the claims.

What is claimed is:

1. A controlled release formulation comprising a flowable delivery system comprising: an organic solvent, a bioactive agent and a biocompatible, biodegradable, non-hydrolyzed linear PLG low-burst copolymer material having a weight average molecular weight of about 15 kilodaltons to about 50 kilodaltons and a polydispersity index of about 1.4 to about 1.8 and which low-burst linear copolymer material is free of a copolymer fraction characterized by a weight average molecular weight of about 4 kDa to about 10 kDa and a polydispersity index of about 1.4 to 2.5.

2. The controlled release formulation of claim 1, wherein the PLG low-burst copolymer material comprises copolymer molecular chains wherein a predominant proportion of the molecular chains comprise predominantly lactate or lactide residues in at least one end domain of each molecular chain and predominantly glycolate or glycolide resides in an internal domain of each molecular chain.

3. The controlled release formulation of claim 1, wherein the bioactive agent is leuprolide, octreotide, brimonidine, latanoprost, latanoprost acid, travoprost, travoprost acid, brinzolamide, dorzolamide, betaxolol, terbinafine, risperidone or rapamycin.

4. The controlled release formulation of claim 1, wherein the bioactive agent is a steroid, a prostaglandin, an analgesic, an antiviral, or an antibiotic.

5. The controlled release formulation of claim 1, wherein the organic solvent is N-methylpyrrolidone, N,N-dimethylformamide, N,N-dimethylacetamide, dimethylsulfoxide, polyethylene glycol 200, polyethylene glycol 300, or methoxypolyethylene glycol 350.

6. The controlled release formulation of claim 1, wherein the bioactive agent is leuprolide or leuprolide acetate and the organic solvent is N-methyl pyrrolidone.

7. The controlled release formulation of claim 1 wherein the content of unreacted lactide and glycolide in the PLG low-burst copolymer material is less than about 1.0 weight % and 0.1 weight % respectively.

8. The controlled release formulation of claim 1, wherein the linear PLG copolymer material has a weight average molecular weight of about 15 kilodaltons to about 21 kilodaltons.

9. The controlled release formulation of claim 1, wherein the linear PLG low-burst copolymer material comprises terminal carboxyl groups that are capped as esters.

10. The controlled release formulation of claim 1, comprising a linear chain extended PLG low-burst copolymer in place of the linear PLG low-burst copolymer material, the linear chain extended PLG low-burst copolymer being the product of the linear PLG low-burst copolymer material and a diol which caps as ester groups the terminal carboxyl groups of two molecules of the linear PLG low-burst copolymer material.

* * * * *